(12) United States Patent
Bibard et al.

(10) Patent No.: US 11,364,039 B2
(45) Date of Patent: Jun. 21, 2022

(54) TOOL HOLDER FOR MODULAR TOOL

(71) Applicant: OSTIUM GROUP, Saint Etienne de Montluc (FR)

(72) Inventors: Léopold Bibard, Saint Etienne de Montluc (FR); Edgard Soquenne, Saint Etienne de Montluc (FR); Vincent Retailleau, Saint Etienne de Montluc (FR)

(73) Assignee: OSTIUM GROUP, Saint Etienne de Montluc (FR)

( * ) Notice: Subject to any disclaimer, the term of this patent is extended or adjusted under 35 U.S.C. 154(b) by 0 days.

(21) Appl. No.: 17/603,912

(22) PCT Filed: Jul. 28, 2020

(86) PCT No.: PCT/EP2020/071304
§ 371 (c)(1),
(2) Date: Oct. 14, 2021

(87) PCT Pub. No.: WO2021/018911
PCT Pub. Date: Feb. 4, 2021

(65) Prior Publication Data
US 2022/0087692 A1    Mar. 24, 2022

(30) Foreign Application Priority Data

Jul. 31, 2019   (EP) .................................... 19305993

(51) Int. Cl.
*A61B 17/16*   (2006.01)
*A61B 17/00*   (2006.01)

(52) U.S. Cl.
CPC ...... *A61B 17/1659* (2013.01); *A61B 17/1668* (2013.01); *A61B 17/1675* (2013.01); *A61B 17/1684* (2013.01); *A61B 2017/00464* (2013.01)

(58) Field of Classification Search
CPC ............ A61B 17/1659; A61B 17/1664; A61B 17/1668; A61B 17/164; A61B 2017/00464
See application file for complete search history.

(56) References Cited

U.S. PATENT DOCUMENTS

| 5,409,492 A | 4/1995 | Jones et al. |
| 5,788,701 A | 8/1998 | McCue |
| 2013/0197489 A1 | 8/2013 | Rister |

FOREIGN PATENT DOCUMENTS

| DE | 9217486 U1 | 2/1993 |
| DE | 202012104364 U1 | 3/2013 |

(Continued)

OTHER PUBLICATIONS

Foreign Communication from a Related Counterpart Application, International Search Report and Written Opinion dated Sep. 17, 2020, International Application No. PCT/EP2020/071301 filed on Jul. 28, 2020.

(Continued)

*Primary Examiner* — Andrew Yang

(57) ABSTRACT

A tool holder for a modular tool is provided in which the tool holder may be releasably coupled to a working part such as a rasp, reamer or impactor. The coupling comprises a slot closed at both extremities, and widening to an entry aperture at one extremity, into which a keyed element of the tool may be inserted, and slid to the opposite extremity of the slot. The modular tool defines a securing pin channel through its body, terminating at the entry aperture such that a securing pin inserted into the channel block the entry aperture and locks the keyed element of the tool in place once inserted.

15 Claims, 5 Drawing Sheets

(56) References Cited

FOREIGN PATENT DOCUMENTS

| | | |
|---|---|---|
| EP | 2077098 A2 | 7/2009 |
| FR | 2903591 A1 | 1/2008 |
| FR | 2910333 A1 | 6/2008 |
| WO | 2021018908 A1 | 2/2021 |
| WO | 2021018910 A1 | 2/2021 |
| WO | 2021018911 A1 | 2/2021 |

OTHER PUBLICATIONS

Foreign Communication from a Related Counterpart Application, International Search Report and Written Opinion dated Dec. 1, 2020, International Application No. PCT/EP2020/071303 filed on Jul. 28, 2020.

Foreign Communication from a Related Counterpart Application, International Search Report and Written Opinion dated Dec. 1, 2020, International Application No. PCT/EP2020/071304 filed on Jul. 28, 2020.

FIG.6
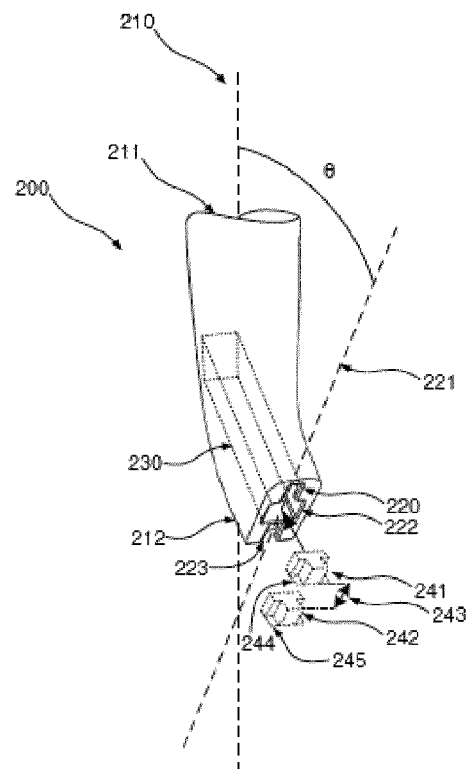
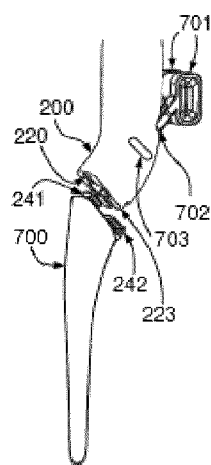
FIG.7a
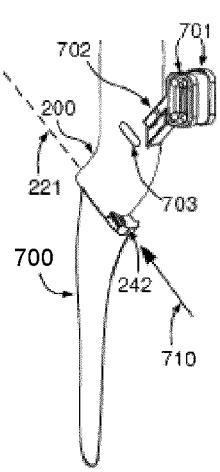
FIG.7b
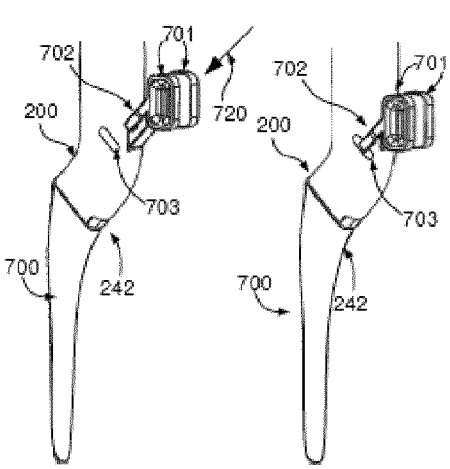
FIG.7c  FIG.7d

TOOL HOLDER FOR MODULAR TOOL

CROSS-REFERENCE TO RELATED APPLICATIONS

The present application is a filing under 35 U.S.C. 371 as the National Stage of International Application No. PCT/EP2020/071304, filed Jul. 28, 2020, entitled "TOOL HOLDER FOR MODULAR TOOL", which claims priority to European Application No. 19305993.8 filed with the European Patent Office on Jul. 31, 2019, both of which are incorporated herein by reference in their entirety for all purposes.

FIELD OF THE INVENTION

The present invention relates to modular tools, and in particular a tool holder element for such tools.

BACKGROUND OF THE INVENTION

The concept of modularity in tools is almost as old as tool use itself. Many ancient tool designs such as hammers, axes, picks and the like comprise a working element fixed to a handle by some means which allows the periodic replacement of one element or the other. Developments in manufacturing processes over the last two hundred years meanwhile have made it possible to develop releasable fixing mechanisms. For example, screw driver heads are commonly available as 6.35 mm (quarter inch) hexagon bits, which may be inserted as required in a standard handle. The bits may be secured magnetically, or by means of a spring loaded ball bearing engaging a groove in the bit. In some contexts meanwhile, the operational constraints extant in that context may tend to lead away from such approaches. In the field of surgical instruments for example, the high forces involved along with sterilisation requirements may tend to indicate an all-in-one approach.

FIG. 1a shows an orthopaedic reamer as known in the state of the art.

As shown in FIG. 1a, a reamer 100 comprises a handle 102 with a strike head 101 and a reamer working surface 103. The reamer 100 is typically made entirely of stainless steel.

Notwithstanding the foregoing, the cost of manufacturing a complete set of stand-alone tools for example as shown in FIG. 1 can be considerable, and even in the field of surgical tools, some attempts at modular tools are known.

In this, as in any field where a solid positive engagement between the handle and further elements is a critical requirement, special consideration must be given to the securing mechanism.

FIG. 1b shows a releasable securing mechanism for modular tools as known in the state of the art.

FIG. 1b shows a conventional securing mechanism known in the art as a "Hudson Fitting". In particular, FIG. 1b shows a male Hudson fitting 110, attached to a tool element 111. The fitting comprises a cylindrical member 113 with a semi-circular channel or groove 114. When the cylindrical member 113 is slid into the corresponding female element, a spring loaded ball bearing 115 engages the channel so as to prevent accidental decoupling. In implementations where uncoupling must be avoided in the presence of a separating force, the ball bearing may be replaced with a removable cotter pin or the like. As shown, the fitting also comprises a flattened flange 112 at the proximal end of the fitting closest to the tool element 111. The flats of this flange may engage corresponding surfaces on the corresponding female element when the coupling is fully inserted, so that rotational forces may be effectively transferred between the two elements of the coupling.

Fittings such as that shown in FIG. 1b have been found unsatisfactory in terms of their ability to provide a solid positive engagement between the handle and further elements, whilst supporting uncoupling with a minimum of force and dexterity when required, yet averting the risk of accidental uncoupling. As such, it is desired to provide an improved coupling addressing some or all of these concerns.

SUMMARY OF THE INVENTION

In accordance with the present invention in a first aspect there is provided a tool holder for a modular tool, the tool holder having a distal end and a proximal end disposed on a longitudinal axis, and comprising a first lateral slot disposed along a second axis, the second axis in the plane of the first axis and being at an angle of between 10 and 80 degrees to the longitudinal axis. The slot widens from top to bottom, the first slot widening to an entry aperture at the distal end of the first slot. The tool holder further comprises a securing pin channel extending though the tool holder and terminating in the entry aperture, such that a securing pin may be inserted through the pin channel so as to trap a keyed element inserted in the widened part of the first slot.

In accordance with a development of the first aspect, the securing pin channel extends along a third axis an angle in the plane of the first and second axes of between 90 degrees to the second axis and 30 degrees to the second axis in the proximal direction.

In accordance with a development of the first aspect, the dimensions of the lateral slot vary along the second axis so that the force required to slide a corresponding keyed element of the tool into the lateral slot increases as the corresponding keyed element of the tool progresses into the slot.

In accordance with a development of the first aspect, the tool holder further comprises a second slot parallel to the first slot.

In accordance with a development of the first aspect the second slot is on the same axis as the first slot, and positioned on the distal side thereof.

In accordance with a development of the first aspect, the second slot provides a lateral opening in the tool holder.

In accordance with a development of the first aspect, the tool holder further comprises one or more features in the vicinity of the entrance of the securing pin channel adapted to engage a resilient member attached to the securing pin such that when inserted fully into the securing channel, the securing pin is resiliently retained in the securing channel.

In accordance with a development of the first aspect, the tool holder further comprises a tongue element provided at a proximal end thereof widening from its junction with the tool holder.

In accordance with a development of the first aspect, the tool holder may be associated with a handle at the proximal end of the tool holder, and a tool at the distal end of the tool holder releasably coupled thereto by means of a keyed element of the tool engaged in the first slot and trapped by the securing pin, where the handle and the tool each have a respective primary axis, whereby the tool holder part is configured to establish a lateral offset between the primary axes.

In accordance with a development of the first aspect, the tool holder and the tool each has a respective primary axis, whereby the tool holder is configured to establish an angular offset between the axes.

In accordance with a development of the first aspect, the tool comprises a rasp or reamer.

In accordance with a development of the first aspect, the tool holder is composed of a synthetic material or a synthetic composite material.

In accordance with a development of the first aspect, the tool holder is composed of a glass fiber reinforced polyarylamide.

BRIEF DESCRIPTION OF THE DRAWINGS

The above and other advantages of the present invention will now be described with reference to the accompanying drawings, for illustration purposes only, in which:

FIG. 6 shows a tool holder for a modular tool in accordance with a further embodiment;

FIG. 7a shows a tool and tool holder in accordance with an embodiment in a first configuration;

FIG. 7b shows a tool and tool holder in accordance with an embodiment in a second configuration;

FIG. 7c shows a tool and tool holder in accordance with an embodiment in a third configuration;

FIG. 7d shows a tool and tool holder in accordance with an embodiment in a fourth configuration;

FIG. 9b shows a side view of tool holder for a modular tool in a variant of the arrangement of FIG. 9a; and FIG. 9c shows a side view of tool holder for a modular tool in a variant of the arrangement of FIG. 9a.

DETAILED DESCRIPTION

Figure 1A:
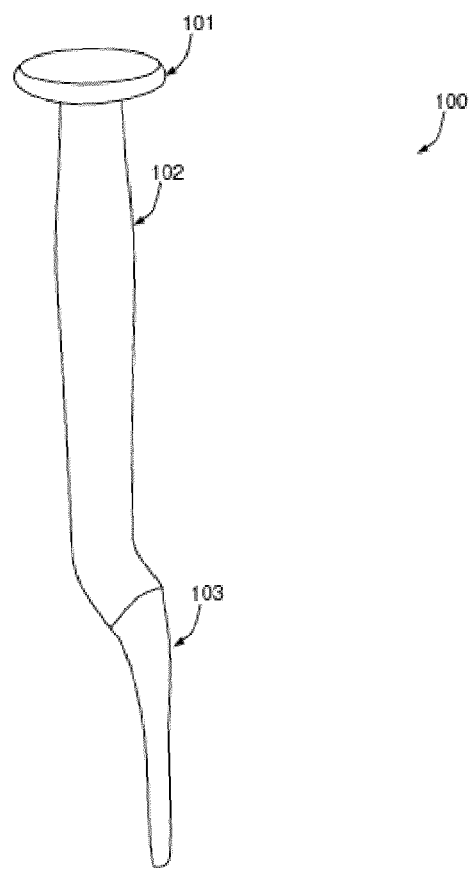
FIG. 1a shows an orthopaedic reamer as known in the state of the art.
Figure 1B:
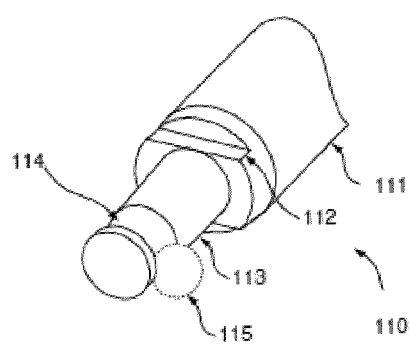
FIG. 1b shows a releasable securing mechanism for modular tools as known in the state of the art.
Figure 2:
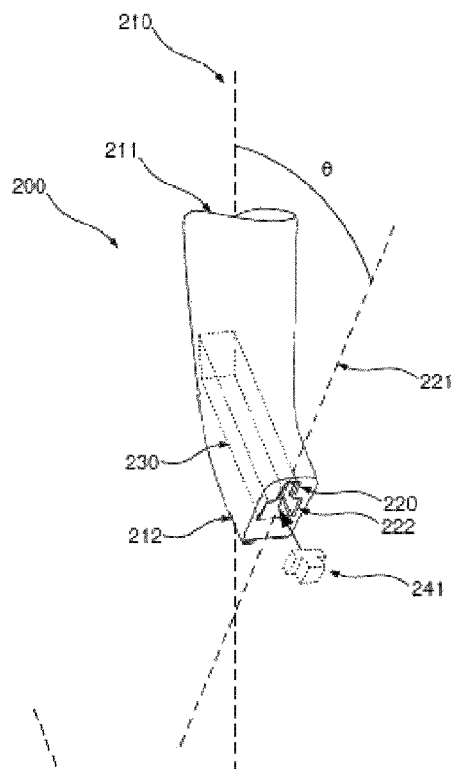
FIG. 2 shows a tool holder for a modular tool in accordance with an embodiment in a first configuration.

FIG. 2 shows a tool holder for a modular tool in accordance with an embodiment in a first configuration.

As shown, the tool holder 200 has a distal end 212 and a proximal end 211 disposed on a longitudinal axis 210. The tool holder comprises a first lateral slot 220 disposed along a second axis 221, the second axis in the plane of the first axis 210 and being at an angle θ of between 10 and 80 degrees to the longitudinal axis 210. The slot widens from top to bottom, and further widens to an entry aperture 222 at the distal end of the first slot 220.

The tool holder further comprises a securing pin channel 230 extending though the tool holder and terminating in the entry aperture 222.

As shown in FIG. 2, a working part is provided with a keyed element 241. The keyed element 241 is dimensioned that it may be inserted into the entry aperture 222. Other regions of the working part are excluded for clarity.

As shown in FIG. 2, the slot 220 defines substantially a T cross section, and the keyed element 241 is shaped correspondingly. This shape achieves the objective of ensuring that the keyed element can only enter or exit the slot through the entry aperture 222, and that once it is slid from the entry aperture to fully engage the slot 220, no force in any direction on the working element with respect to the tool holder will separate the working element secondary element from the tool holder. The skilled person will recognise that the keyed element and corresponding slot may have any form complying with the general requirement that it widens from the distal end towards the proximal end. As such, it may form a wedge, dovetail or T section as described above. It may furthermore be circular, elliptical, rectangular, square, or any other form. The keyed element will generally constitute an extrusion of the chosen cross section from one side to the other. In certain embodiments, the keyed element may taper from one side to the other. Where this is the case the slot may taper from side to side correspondingly. Where this is the case, the slot may be defined as being deeper from side to side that the length from side to side of the corresponding keyed element. On this basis, the tapering walls of the keyed element will engage the sides of the keyed element before the end of the keyed element reached the lateral extremity of the slot. By this means, the slot will become progressively tighter as the keyed element is inserted, and a firm insertion without any play between the handle and secondary element may be achieved by pushing the keyed element fully into the slot.

The working part may comprise a tool. The tool may comprise a surgical instrument. More particularly for example, the tool may be for surgery of the orthopaedic surgery or bone traumatology. Still more particularly for example the tool may comprise a rasp or reamer or impactor.

The disposition of the first lateral slot 220 disposed along a second axis 221, the second axis in the plane of the first axis 210 and being at an angle θ of between 10 and 80 degrees to the longitudinal axis 210 means that the application of a force along the tool holder through the working element will force the working element more deeply in to the slot to abut the end wall thereof, rather than tending to push the working element out of the slot.

Figure 3:
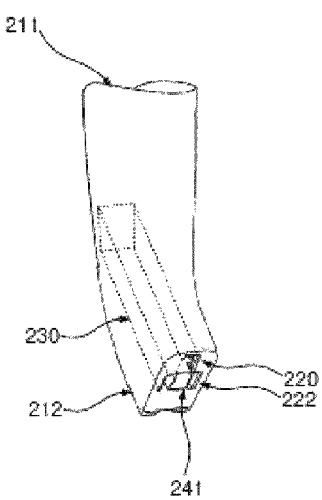
FIG. 3 shows a tool holder for a modular tool in accordance with an embodiment in a second configuration.

FIG. 3 shows a tool holder for a modular tool in accordance with an embodiment in a second configuration.

The tool holder of FIG. 3 comprises substantially the same elements as described with reference to FIG. 2. As shown in FIG. 3, the keyed element 241 has been inserted into the entry aperture 222. Other regions of the working part are excluded for clarity.

Figure 4:
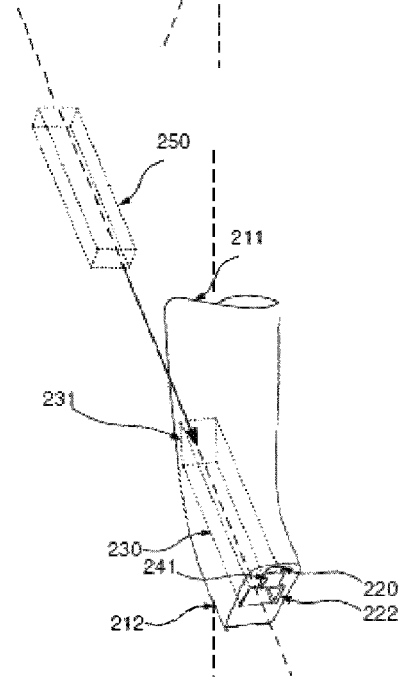
FIG. 4 shows a tool holder for a modular tool in accordance with an embodiment in a third configuration.

FIG. 4 shows a tool holder for a modular tool in accordance with an embodiment in a third configuration.

The tool holder of FIG. 4 comprises substantially the same elements as described with reference to FIGS. 2 and 3. As shown in FIG. 4, the keyed element 241 has been slid upward into the proximal extremity of the slot 220, away from the entry aperture 222. Since the keyed element 241 as shown widens from its base in correspondence to the widening of the slot 220, once slid upward in this manner the keyed element is trapped in the slot, the only possible path of exit being back through the entry aperture 222.

Optionally, the dimensions of the lateral slot may vary along the second axis so that the force required sliding a corresponding keyed element into the lateral slot increases as the corresponding keyed element of the tool progresses into the slot.

Meanwhile, a securing pin 250 is positioned at a proximal entrance 231 of securing pin channel 230, which terminates at the distal end of the tool holder with the entry aperture 222, ready for insertion. The securing pin channel extends along a third axis, the third axis being at an angle in the plane of the first and second axes of between 90 degrees to the second axis and 30 degrees to the second axis in the proximal direction.

As shown, the securing pin 250 is substantially rectangular in cross section. In other embodiments, the securing pin may have any extruded form including a prism having any number of sides. Some or all sides may be curved. As such, the securing pin may be, for example, cylindrical, semicircular, triangular, square, rectangular and so on.

Since the slot 220 widens from the distal end 212 towards the proximal end 211, a correspondingly formed keyed element 241 may be slid into the slot laterally as shown in FIG. 4, but once in position, will not be movable along the axis of the tool holder, i.e. towards or away from the distal end of the tool holder, but only back or forth along the axis of the slot.

Other regions of the working part are excluded for clarity.

Figure 5:
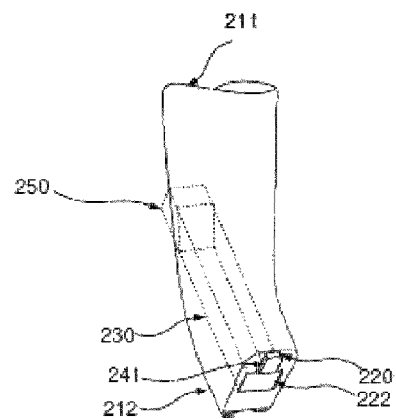
FIG. 5 shows a tool holder for a modular tool in accordance with an embodiment in a fourth configuration.

FIG. 5 shows a tool holder for a modular tool in accordance with an embodiment in a fourth configuration.

The tool holder of FIG. 5 comprises substantially the same elements as described with reference to FIGS. 2, 3 and 4. As shown in FIG. 5, the securing pin 250 has been inserted through the pin channel 230 so as to fill the entry aperture 222, thereby trapping the keyed element in the slot 220.

FIG. 6 shows a tool holder for a modular tool in accordance with a further embodiment.

The tool holder of FIG. 6 comprises substantially the same elements as described with reference to FIG. 2 above. As shown in FIG. 6, the tool holder 200 comprises a second slot 223 parallel to the first slot 220. Where this configuration is adopted, it may be considered that the first and second slots define a single continuous slot, which is interrupted by an intermediate wall, and an end wall at the proximal extremity. The second slot 223 may widen from top to bottom in a manner similar to the first slot 220. The second slot 223 may widen from top to bottom identically to the first slot 220. As shown, while the first slot widens to an entry aperture 222 at the distal end of the first slot 220, the second slot 223 opens laterally at the distal extremity of the tool holder 200. As shown, the second slot is on the same axis 221 as the first slot. In other embodiments, the second slot may be situated in a further axis in parallel with the axis 221. Where the second slot does not open at the edge of the tool holder as shown, it may open to a further respective entry aperture in the same way as the first slot. It will be appreciated that any number of slots, and corresponding keyed elements may be provided on this basis. Distributing slots across the distal surface of the tool holder provides multiple connection points with the tool, and as such will tend to stabilize the connection between the tool and tool holder.

FIGS. 7a, 7b, 7c and 7d illustrate the steps of insertion of a tool into a tool holder as described above, and provide further details relating to the operation of the securing pin.

FIG. 7a shows a tool and tool holder in accordance with an embodiment in a first configuration.

As shown, the tool holder 200 has a distal end 212 and a proximal end 211 disposed on a longitudinal axis 210. The tool holder comprises a first lateral slot 220 disposed along a second axis 221, the second axis in the plane of the first axis 210 and being at an angle θ of between 10 and 80 degrees to the longitudinal axis 210. The slot widens from top to bottom, and further widens to an entry aperture 222 at the distal end of the first slot 220.

The tool holder further comprises a securing pin channel 230 extending though the tool holder and terminating in the entry aperture 222.

As shown in FIG. 7a, a working part 700 is provided with a first keyed element 241 and second keyed element 242, substantially as described above.

The tool holder 200 of FIG. 7a meanwhile comprises a first slot 220 and second slot 223 substantially as described above.

The tool holder comprises a pin channel (not shown) substantially as described above, into which a securing pin 702 is partially inserted. As shown, the securing pin further comprises optional opposing pinch plates 701, which operate optional grasping members 702 positioned either side of the body of the of the tool holder and pivotally mounted on the securing pin. The grasping members are biased towards the securing pin. This biasing might be achieved by the provision of a spring or other resilient member. It may also be achieved by forming the grasping members and securing pin in a single piece, of a material which exhibits resilience when suitably formed.

As shown, the tool holder 200 further comprises optional indentations 703 on either side thereof, positioned either side of the pin channel entrance so that that when the securing pin is fully inserted in the pin channel, each grasping member 702 may engage a respective indentation 703.

As an alternative, features similar to indentations 703 may be provided on the inside of the securing pin channel, and the securing pin provided with protuberances adapted to engage these features when the securing pin is inserted into the securing pin channel. The securing pin may be split partially along its lengths so as to provide two parallel portions resiliently joined at the distal end of the securing pin, so that the two portions may be squeezed together, for example by means of the pinch plates 703 during insertion, such that when allowed to resume their unconstrained configuration, the protuberances engage the features.

It will be appreciated that other equivalent arrangement may be envisaged, for example with indentations on the securing pin and protuberances on the inside or outside of the interface part, and so on.

As such the tool holder may comprise one or more features in the vicinity of the entrance of the securing pin channel adapted to engage a resilient member attached to the securing pin such that when inserted fully into the securing channel, the securing pin is resiliently retained in the securing channel.

Optionally, the securing pin and/or securing pin channel may have varying dimensions along the lengths, so as to restrict or inhibit the movement of the securing pin in the securing pin channel as it approaches a fully inserted position. Optionally, the securing pin and/or securing pin channel may have varying dimensions along the lengths, so as to restrict or inhibit the movement of the securing pin in the securing pin channel as it approaches a retracted position, so as to reduce the likelihood of the securing pin being accidentally removed from the securing pin channel, and possibly dropped or mislaid.

Generally, the tool holder may provide one or more features in the vicinity of the entrance of the securing pin channel adapted to engage a resilient member attached to the securing pin such that when inserted fully into the securing channel, the securing pin is resiliently retained in the securing channel. It will be appreciated that there is provided a working part having features in correspondence to the tool holder of the present invention, and in particular to the releasable coupling thereof. In particular, there is provided a working element 700 for a modular tool, the working element having a distal end and a proximal end disposed on a longitudinal axis. The working element comprises a first keyed element 241 and a second keyed element 242 widening in a distal direction (so as not to be free to fall out of the slot in the distal direction once inserted), disposed along a second axis 221, and separated by a gap 243. By this means the working part may be secured in a corresponding tool holder 200 for example as described herein by inserting the first keyed element and said second keyed elements into corresponding slots 220, 223 defined in said tool holder 200, and inserting a securing pin 702 through a securing pin channel 230 extending though said tool holder 200 and terminating in said gap 243 so as to trap a keyed element 241 inserted in said first slot.

Optionally, either or both of the keyed elements 241, 242 may be provided with a respective end plate 244, 245. Such end plates may serve to provide a solid end stop limiting and controlling the insertion of the keyed element into the slot. In particular, this approach may be used as well as or instead of the provision of the end wall and/or intermediate wall of the slot as described above.

FIG. 7b shows a tool and tool holder in accordance with an embodiment in a second configuration.

As shown, the working part 700 and tool holder 200 have been aligned so that the first keyed element 241 and second keyed element 242 are in the axis 221 of the first slot 220 and second slot 223. The working part 700 and tool holder 200 are slightly offset in a distal direction so that the first keyed element 241 has been inserted into the entry aperture 222, while the second keyed element 242 is outside, but aligned with the second slot 223.

Once in this configuration, a force along the axis 221 as shown by arrow 710 will cause the working part 700 and tool holder 200 to fully engage.

FIG. 7c shows a tool and tool holder in accordance with an embodiment in a third configuration.

As shown, a force has been exerted along the axis 221 as shown by arrow 710 in FIG. 7b, causing the working part 700 and tool holder 200 to fully engage.

As such, the first keyed element 241 is fully inserted into the first slot 220, clearing the entry aperture 222, while the second keyed element 242 is fully inserted into the second slot 223.

Once in this configuration, the securing pin 702 may be fully inserted into the pin channel (not shown) substantially as described above, by exertion of a force along the axis of the pin channel as represented by the arrow 720.

FIG. 7d shows a tool and tool holder in accordance with an embodiment in a fourth configuration.

As shown, the securing pin 702 has been fully inserted into the pin channel (not shown) substantially as described above.

As shown, the grasping members 702 positioned either side of the body of the of the tool holder and pivotally mounted on the securing pin have engaged the indentations 703 on either side of the tool holder, either by an automatic latching operation enabled by the form of the grasping members, or by manual operation of the pinch plates 701 as described above.

In this configuration, the securing pin is positively engaged in the securing channel, and by securing the entry aperture 222 as described above ensures that no movement of the working part 700 with respect to the tool holder 200 is possible in any direction. Furthermore, the securing pin itself is locked in the securing channel by the grasping members so that without the deliberate action of a user to disengage the grasping members and remove the securing pin, the working element and tool holder are indissociable.

As such, the sequence of configurations 7a, 7b, 7c and 7d represent a series of simple manipulations which may be undertaken by a user. For example, the user may grip the tool holder in one hand with their thumb resting on the end of the securing pin, while gripping the working element in the other hand. The user may then bring the tool holder and working element together, and engage the keyed elements of the working element in the corresponding slots of the tool holder, and slide the working element to the end of the available travel in the slots, before pushing the securing pin into position with the thumb so as to lock the working element in place.

To further facilitate these actions, the elements may be knurled, grooved, provided with a non-slip coating or otherwise treated to improve the users grip thereon. In particular the securing pin may be knurled, grooved, provided with a non-slip coating or provided with a loop, hook, or other formation adapted to engage the users thumb such that the securing pin may be both pushed forward to block the entry aperture, and pulled back to unblock the entry aperture with the users thumb.

Meanwhile, when pinch plates 701 are brought together, for example by being pinched together by the index finger and thumb of a user, the grasping members are separated, so that the securing pin may be pulled back out of the pin channel, freeing the working part 700 with respect to the tool holder 200, and making it possible for the two parts to be separated in the reverse of the sequence of FIGS. 7c, 7b and 7a.

Figure 8:
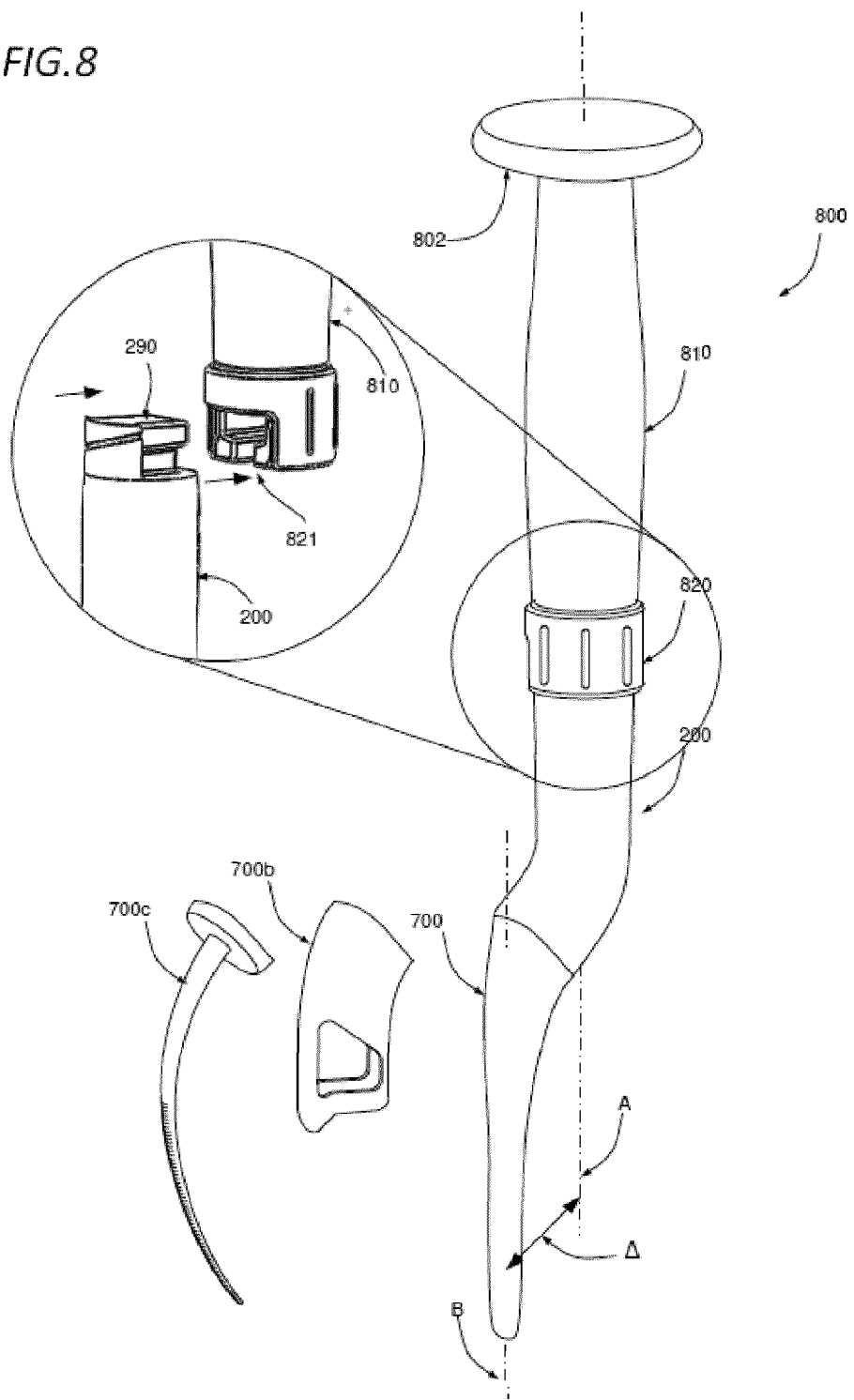
FIG. 8 shows a tool in accordance with an embodiment.

FIG. 8 shows a tool in accordance with an embodiment.

As shown, there is provided a modular tool 800 comprising a handle 810, and a tool holder 200 substantially as described above. The handle 810 comprises a releasable coupling comprising by way of example a threaded ring 820, the threads of the ring engaging an external helical thread of the cylindrical member of the handle 810. The threaded ring 820 is rotatable about the distal end of the member between an extended position as shown in FIG. 7 which the ring obstructs a slot 821 opening on one periphery of the distal end of the body, and a retracted position as shown in the emphasised section 850 in which the ring leaves the slot 821 opening on one periphery of the distal end of the body unobstructed, into which a tongue element 290 at the proximal extremity of the tool holder may be inserted. When the ring is rotated about the cylindrical member, it progresses along the length thereof and whilst progressing lengthwise and rotating, obstructs a slot 821 as shown in FIG. 7 to trap the tool holder in place.

The handle may optionally be provided with an angle datum such as a radial line on the guard plate, or a radial lumen through which a bar may by inserted.

As such the tool holder may further comprise a tongue element provided at a proximal end thereof, the tongue being widening from its junction with the tool holder.

The tool holder may be associated with a handle at the proximal end of the tool holder, and a tool at the distal end of the tool holder releasably coupled thereto by means of a tongue of the tool engaged in the first slot and trapped by the securing pin, where the handle 810 has a primary axis A and the tool 700 has a primary axis B, whereby the tool holder 200 is configured to establish a lateral offset A between the two primary axes.

The tool holder may additionally or alternatively establish an angular offset between the axes.

Alternatively a Hudson fitting as known in the state of the art, or any other convenient mechanism may be used to secure the tool holder to the handle.

Meanwhile, the tool holder comprises at a distal end a first lateral slot disposed along a second axis, the second axis in the plane of the first axis and being at an angle of between 10 and 80 degrees to the longitudinal axis, the slot widening from top to bottom, the first slot widening to an entry aperture at the distal end of the first slot, the tool holder further comprising a securing pin channel extending though the tool holder and terminating in the entry aperture, such that a securing pin may be inserted through the pin channel so as to trap a keyed element inserted in the widened part of the first slot, substantially as described above, to provide a releasable coupling between the tool holder 200 and working part 700. Any of the other variants or optional features presented above may be adopted, or not, in a modular tool along the lines of that of FIG. 8, as appropriate to the use case.

As shown, the handle further comprises an optional guard plate 802 at the proximal end thereof. Such a guard plate may serve to protect the hand of a user when gripping the handle 820 from blows struck against the proximal end thereof with a hammer, mallet or the like, for example where the tool or working part 700 is a chisel, reamer or other such tool requiring a percussive application.

One field in which a handle as described may be appropriate is that of surgical instruments, such that the modular tool as a whole may comprise or constitutes a surgical instrument. More particularly, the modular tool may be for orthopaedic surgery or bone traumatology. More particularly, the modular tool may be for surgery of the hip, shoulder or knee. More particularly, as shown, the working part 700, and thus the modular tool as a whole 700 comprises a rasp or reamer or impactor. It will be appreciated that in line with the many fields of application and associated tool types that may be envisaged, many different possible working parts 700 may be envisaged, for use with a single handle in accordance with embodiments as described above. Further examples of possible working parts, and resulting modular tools, include a curved rasp 700b, osteotome 700c and many other tools as will readily occur to the skilled person.

The tool holder of the present invention may be formed of any material. In particular, it may be formed of steel, aluminium, titanium or any other suitable metal or alloy. It may also be formed of a thermoplastic or other synthetic material. It may in particular be formed from a polyamide, for example a polyarylamide. The synthetic material may comprise additional components such as a filler, swelling agent and the like. It may still further be formed of a synthetic composite material, comprising a glass, carbon fibre, carbon nanoparticle or any other material exhibiting a high tensile strength, in a matrix of a synthetic material, such as any of those listed above. In certain embodiments, the tool holder may be composed of a glass fibre reinforced polyarylamide, such as for example that marketed by the Solvay corporation under the trademark "Ixef GS 1022".

The tool holder may be formed of different materials in different regions, including metal parts and synthetic parts. The handle may also comprise voids for the purpose of economy of material, reduced weight and so on.

Where the tool holder is incorporated in a modular tool as shown in FIG. 8, the working part and/or handle may each be composed of the materials mentioned above. In some embodiments, the handle, tool holder and working part may all be composed of the same material.

In certain embodiments, the angle of insertion of the working part in the tool holder may be envisaged.

Figure 9A:
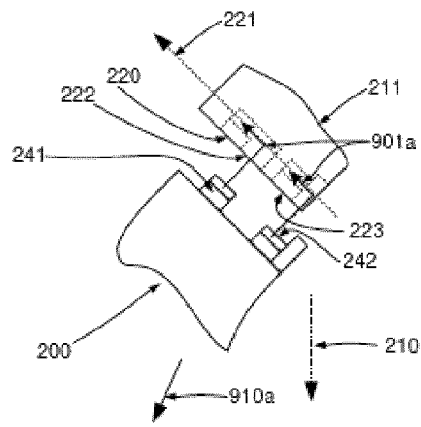
FIG. 9a shows a side view of tool holder for a modular tool substantially as described above with reference to FIG. 2.

FIG. 9a shows a side view of tool holder for a modular tool substantially as described above with reference to FIG. 2.

In particular, the tool holder 200 comprises a first lateral slot 220 disposed along a second axis 221, the second axis in the plane of the first axis 210 and being at an angle $\theta$ of approximately 45 degrees to the longitudinal axis 210. The slot widens from top to bottom, and further widens to an entry aperture 222 at the distal end of the first slot 220. The working part is provided with a keyed element 241. The keyed element 241 is dimensioned that it may be inserted into the entry aperture 222.

The "push and slide" insertion action implied by the arrangement of FIG. 9a is represented by arrows 901a.

As discussed above, the disposition of the first lateral slot 220 disposed along a second axis 221, the second axis in the plane of the first axis 210 and being at an angle $\theta$ of between 10 and 80 degrees to the longitudinal axis 210 means that the application of a force along the tool holder through the working element will force the working element more deeply in to the slot to abut the end wall thereof, rather than tending to push the working element out of the slot.

While as discussed with respect to FIG. 2 the axis 210 is presented as being aligned with the axis of a notional handle which may be provided as discussed herein, it will be appreciated that depending on the shape of the tool holder on one hand, and the tool on the other, a working longitudinal axis 910a may diverge from the axis of the handle as shown in FIG. 9a, and that is with respect to this axis that an angle $\theta$ of between 10 and 80 degrees may be established to achieve the benefit whereby the application of a force along the tool holder through the working element will force the working element more deeply in to the slot to abut the end wall thereof, rather than tending to push the working element out of the slot.

Figure 9B:
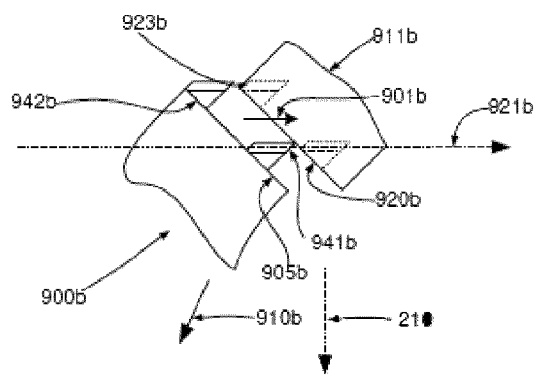

FIG. 9b shows a side view of tool holder for a modular tool in a variant of the arrangement of FIG. 9a.

In particular, the tool holder 900b (corresponding substantially to toolholder 200 as described above) comprises a first lateral slot 920b corresponding substantially to first lateral slot 220 as described above) disposed along a second axis 921b (corresponding substantially to second axis 221 as described above), the second axis in the plane of the first axis 210 and being at an angle $\theta$ of approximately 70 degrees to the longitudinal axis 910b. The working part is provided with a keyed element 241.

The insertion action implied by the arrangement of FIG. 9b is represented by arrows 901b.

It may be noted that in the embodiment of FIG. 9b the keyed elements 941b and 942b corresponding to elements 241 and 242 as described above are formed with their respective keyed parts at an angle to the end surface of the tool holder 905b so that as represented by arrow 901b the keyed elements may be slid directly into their corresponding slots in a single linear motion.

Figure 9C:
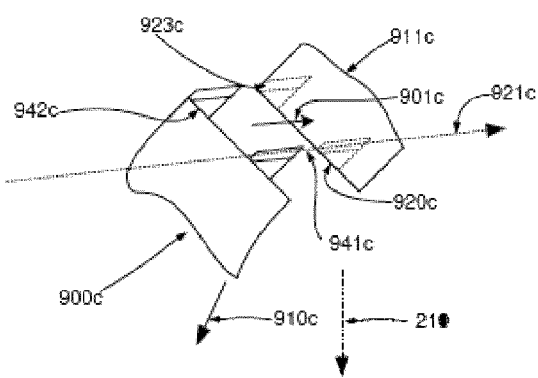

FIG. 9c shows a side view of tool holder for a modular tool in a variant of the arrangement of FIG. 9a.

In particular, the tool holder 900c (corresponding substantially to toolholder 200 as described above) comprises a first lateral slot 920c corresponding substantially to first lateral slot 220 as described above) disposed along a second axis 921c (corresponding substantially to second axis 221 as described above), the second axis in the plane of the first axis 210 and being at an angle $\theta$ of approximately 45 degrees to the longitudinal axis 910c (and 80 degrees to the longitudinal axis of the notional handle 210). The working part is provided with a keyed element 241.

The insertion action implied by the arrangement of FIG. 9*c* is represented by arrows 901*c*.

It may be noted that in the embodiment of FIG. 9*b* the keyed elements 941*b* and 942*b* corresponding to elements 241 and 242 as described above are formed with their respective keyed parts at an angle to the end surface of the tool holder 905*b* so that as represented by arrow 901*b* the keyed elements may be slid directly into their corresponding slots in a single linear motion.

As such, there is provided a tool holder for a modular tool in which the tool holder may be releasably coupled to a working part such as a rasp, reamer or impactor. The coupling comprises a slot closed at both extremities, and widening to an entrance aperture at one extremity, into which a keyed element of the tool may be inserted, and slid to the opposite extremity of the slot. The modular tool defines a securing pin channel through its body, terminating at the entry aperture such that a securing pin inserted into the channel block the entry aperture and locks the keyed element of the tool in place once inserted.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A tool holder for a modular tool, said tool holder having a distal end and a proximal end disposed on a first longitudinal axis; said tool holder comprising a first lateral slot disposed along a second axis, said second axis in the plane of the first axis and being at an angle of between 10 and 80 degrees to said first axis, said slot widening from top to bottom, said first slot widening to an entry aperture at the distal end of the first slot, said tool holder further comprising a securing pin channel extending through said tool holder and terminating in said entry aperture, such that a securing pin may be inserted through said pin channel so as to trap a keyed element inserted in the widened part of said first slot.

2. The tool holder of claim 1, wherein said securing pin channel extends along a third axis, said third axis being at an angle in the plane of the first and second axes of between 90 degrees to the second axis and 30 degrees to the second axis in the proximal direction.

3. The tool holder of claim 1 wherein the dimensions of said lateral slot vary along said second axis so that the force required to slide a corresponding keyed element of said tool into said lateral slot increases as said corresponding keyed element of said tool progresses into said slot.

4. The tool holder of claim 1 comprising a second slot parallel to the first slot.

5. The tool holder of claim 4 wherein said second slot is on the same axis as the first slot, and positioned on the distal side thereof.

6. The tool holder of claim 4 wherein said second slot provides a lateral opening in said tool holder.

7. The tool holder of claim 1 further comprising one or more features in the vicinity of the entrance of said securing pin channel adapted to engage a resilient member attached to said securing pin such that when inserted fully into said securing channel, said securing pin is resiliently retained in said securing channel.

8. The tool holder of claim 1 further comprising a tongue element provided at a proximal end of said tool holder, said tongue being widening from its junction with the tool holder.

9. The tool holder of claim 1 wherein said tool holder may be associated with a handle at the proximal end of the tool holder, and a tool at the distal end of the tool holder releasably coupled thereto by means of a tongue of said tool engaged in said first slot and trapped by said securing pin.

10. The tool holder of claim 9 where said handle and said tool each have a respective primary axis, whereby the tool holder part is configured to establish a lateral offset between said primary axes.

11. The tool holder of claim 9 wherein said tool holder and said tool each has a respective primary axis, whereby the tool holder is configured to establish an angular offset between said axes.

12. The tool holder of claim 1 wherein said tool comprises a rasp or reamer.

13. The tool holder of claim 1 wherein said tool holder is composed of a synthetic material or a synthetic composite material.

14. The tool holder of claim 13 wherein said tool holder is composed of a glass fiber reinforced polyarylamide.

15. A modular tool comprising the tool holder according to claim 1 and a working element having a distal end and a proximal end disposed on a longitudinal axis, said working element comprising a first keyed element and a second keyed element, said first keyed element and said second keyed element being disposed along a second axis, and separated by a gap, said first keyed element and said second keyed element widening in a distal direction, whereby said working part may be secured in a corresponding tool holder by inserting said first keyed element and said second keyed elements into corresponding slots defined in said tool holder, and inserting a securing pin through a securing pin channel extending though said tool holder and terminating in said gap so as to trap a keyed element inserted in the widened part of said first slot.

* * * * *